(12) United States Patent
Tokunaga et al.

(10) Patent No.: US 8,475,638 B2
(45) Date of Patent: Jul. 2, 2013

(54) BIOSENSOR

(75) Inventors: Hiroyuki Tokunaga, Ehime (JP); Shoji Miyazaki, Ehime (JP); Eriko Yamanishi, Ehime (JP)

(73) Assignee: Panasonic Corporation, Osaka (JP)

( * ) Notice: Subject to any disclaimer, the term of this patent is extended or adjusted under 35 U.S.C. 154(b) by 0 days.

(21) Appl. No.: 12/823,676

(22) Filed: Jun. 25, 2010

(65) Prior Publication Data

US 2010/0258438 A1   Oct. 14, 2010

Related U.S. Application Data

(63) Continuation of application No. 10/297,888, filed as application No. PCT/JP02/03600 on Apr. 11, 2002.

(30) Foreign Application Priority Data

Apr. 16, 2001   (JP) .................................. 2001-116580

(51) Int. Cl.
   *G01N 27/327*   (2006.01)
(52) U.S. Cl.
   USPC ...................................... 204/403.14; 435/14
(58) Field of Classification Search
   USPC ........... 204/403.01, 403.14; 205/792; 435/10, 435/287.9, 14, 25, 26, 40.5, 287
   See application file for complete search history.

(56) References Cited

U.S. PATENT DOCUMENTS

| | | | |
|---|---|---|---|
| 4,172,770 A | 10/1979 | Semersky et al. | |
| 5,120,420 A | 6/1992 | Nankai et al. | |
| 5,192,415 A | 3/1993 | Yoshioka et al. | |
| 5,264,103 A | 11/1993 | Yoshioka et al. | |
| 5,512,159 A | 4/1996 | Yoshioka et al. | |
| 5,582,697 A | 12/1996 | Ikeda et al. | |
| 6,004,441 A | 12/1999 | Fujiwara et al. | |
| 6,258,229 B1 * | 7/2001 | Winarta et al. | 204/403.04 |
| 6,299,757 B1 * | 10/2001 | Feldman et al. | 205/775 |
| 6,309,526 B1 | 10/2001 | Fujiwara et al. | |
| 6,875,327 B1 | 4/2005 | Miyazaki et al. | |

FOREIGN PATENT DOCUMENTS

| | | |
|---|---|---|
| EP | 0 537 761 A2 | 4/1993 |
| EP | 1 152 239 A1 | 11/2001 |
| JP | 61-294351 A | 12/1986 |
| JP | 01291153 A | 11/1989 |
| JP | 03075552 A | 3/1991 |
| JP | 04357452 A | 12/1992 |

(Continued)

OTHER PUBLICATIONS

US Office Action for U.S. Appl. No. 10/297,288, Dec. 21, 2010, Panasonic Corporation.

(Continued)

*Primary Examiner* — J. Christopher Ball
(74) *Attorney, Agent, or Firm* — RatnerPrestia (57) ABSTRACT

In a biosensor that detects introduction of a sample liquid into a specimen supply path using a detecting electrode, a means of improving accuracy of detection is provided. The biosensor has: an electrode system including measuring electrode, counter electrode, and detecting electrode on first electrically insulating support; specimen supply path for introducing the sample liquid; and reagent layer used for quantifying a substrate contained in the sample liquid. The means is characterized in that detecting electrode is spaced from measuring electrode by a distance sufficient for the sample liquid to sufficiently cover measuring electrode before the sample liquid reaches detecting electrode.

14 Claims, 6 Drawing Sheets

FOREIGN PATENT DOCUMENTS

| | | |
|---|---|---|
| JP | 05-340915 A | 12/1993 |
| JP | 06109688 A | 4/1994 |
| JP | 06229970 A | 8/1994 |
| JP | 08320304 A | 12/1996 |
| JP | 09-043189 A | 2/1997 |
| JP | 09189675 A | 7/1997 |
| JP | 2000-065778 A | 3/2000 |
| JP | 2001-066279 A | 3/2001 |
| JP | 2001-208715 A | 8/2001 |
| JP | 2001-305096 A | 10/2001 |
| JP | 2001305093 A | 10/2001 |
| JP | 2001330581 A | 11/2001 |
| JP | 2001-356108 A | 12/2001 |
| WO | WO 00/73778 A1 | 12/2000 |

OTHER PUBLICATIONS

Supplementary European Search Report for EP 02 71 8528, Jun. 16, 2009.

European Search Report for Application No. EP 10 16 2536, Jul. 26, 2010, Panasonic Corporation.

* cited by examiner

BIOSENSOR

This application is a continuation of U.S. patent application Ser. No. 10/297,888, filed May 6, 2003, which is incorporated herein by reference.

TECHNICAL FIELD

The present invention relates to a biosensor that quantifies a substrate contained in a sample liquid.

BACKGROUND ART

A biosensor is a sensor that utilizes the molecule-identifying function of a biological material, e.g. a microorganism, enzyme, antibody, DNA, and RNA, and applies such a biological material as a molecule-identifying element. In other words, the biosensor utilizes the reaction occurring when an immobilized biological material identifies a target substrate, oxygen consumed by breathing of living organisms, enzyme reaction, luminescence, and the like. Among biosensors, practical use of enzyme sensors is developing. For example, enzyme sensors for glucose, lactic acid, uric acid, and amino acid find applications in medical instrumentation and food processing industry.

In an enzyme sensor, for example, electrons generated by the reaction of a substrate contained in a sample liquid, i.e. an analyte, with an enzyme or the like reduce an electron acceptor and a measuring device electrochemically measures the amount of the reduced electron acceptor. Thus, quantitative analysis of the analyte is performed. An example of such a biosensor is a sensor proposed in Patent Application No. PCT/JP00/08012.

Figures 4A, 4B:
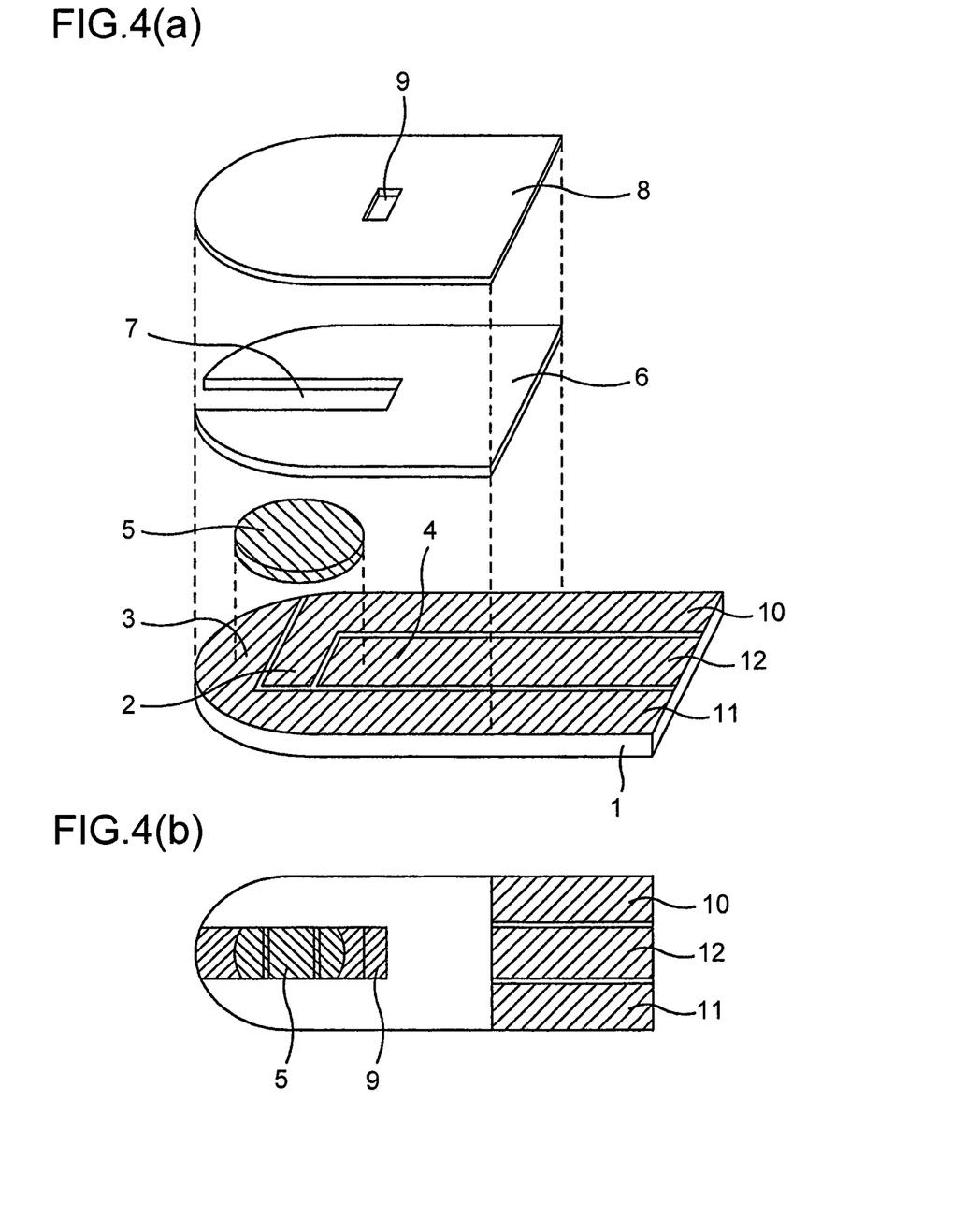
FIG. 4 is an exploded perspective view and a top view of a conventional biosensor.

In this biosensor, as shown in FIG. 4, electrically insulated board 1 made of polyethylene terephthalate or other materials has measuring electrode 2 (also referred to as a "working electrode"), counter electrode 3, and detecting electrode 4 that are made of electrically conductive materials and formed in proximity to one another on the electrically insulated board. Formed on these electrodes is regent layer 5 that contains an enzyme specifically reacting with a particular component in the sample liquid, an electron carrier, a water-soluble polymer, and the like.

Laminated thereon and bonded thereto are spacer 6 having a notch for forming analyte feed passage 7, and cover 8 (second electrically insulated board) having air vent 9. One end of the notch in spacer 6 is in communication with air vent 9 provided through cover 8.

Described hereinafter is a system of checking for suction of an analyte when the content of a substrate in a sample liquid, i.e. the analyte, is determined using a conventional biosensor of such a structure.

First, a sample liquid is supplied to the inlet of analyte feed passage 7 while a constant voltage is applied between counter electrode 3 or measuring electrode 2 and detecting electrode 4 by a measuring device (not shown) coupled to the biosensor. The sample liquid is sucked into analyte feed passage 7 by capillarity, passes over counter electrode 3 and measuring electrode 2, and reaches detecting electrode 4. Then, dissolution of reagent layer 5 starts. At this time, the measuring device detects electrical changes occurring between counter electrode 3 or measuring electrode 2 and detecting electrode 4 and starts measuring operation.

Figure 5:
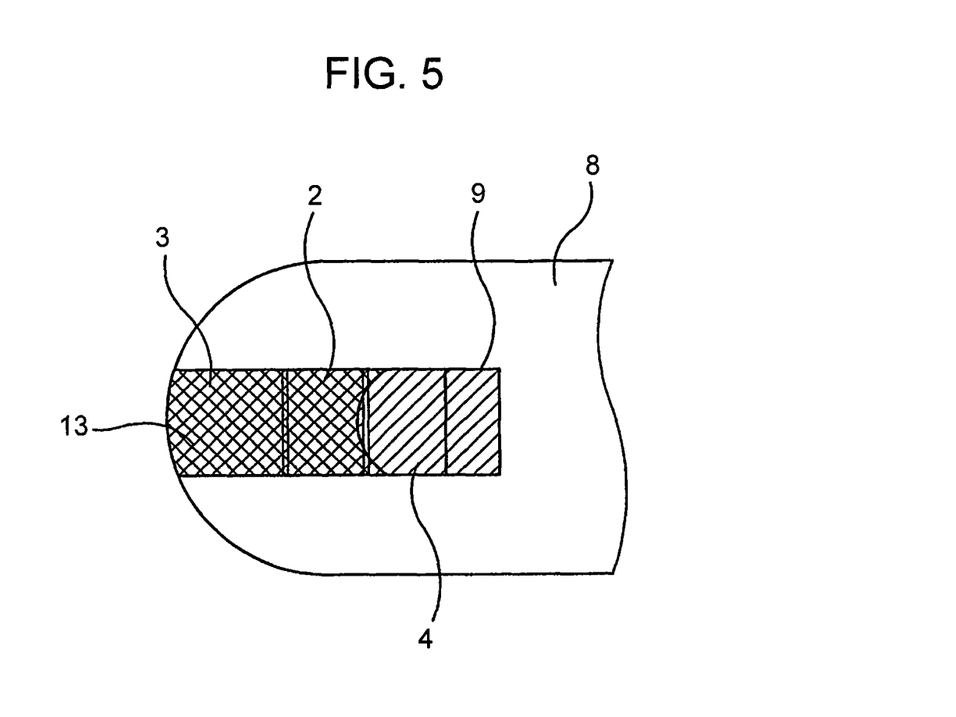
FIG. 5 is a drawing showing how a sample liquid is introduced into an analyte feed passage.
Figure 6:
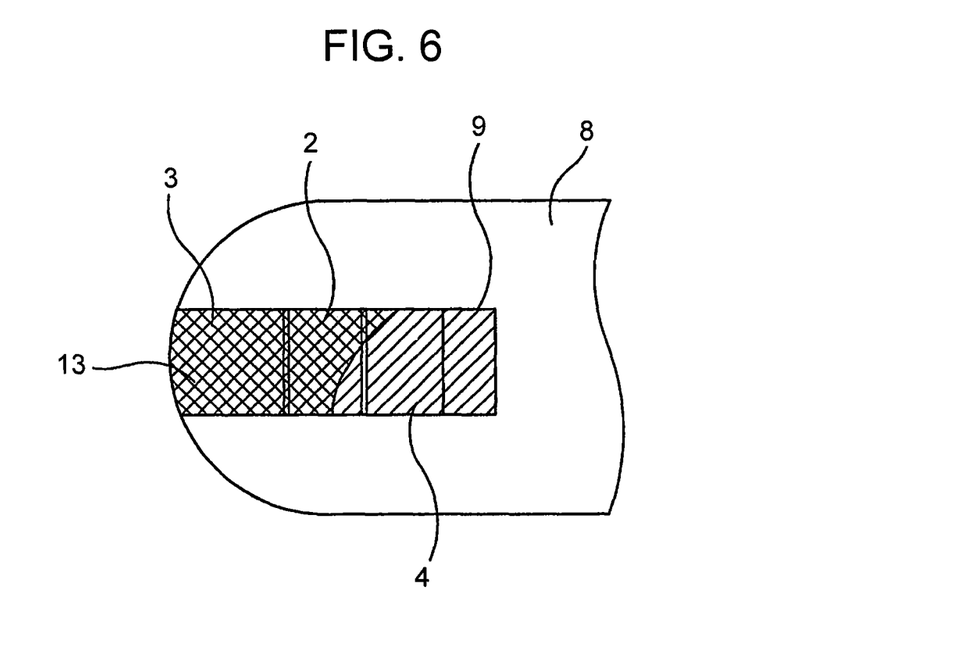
FIG. 6 is a drawing showing how a sample liquid is introduced into an analyte feed passage.
Figure 7:
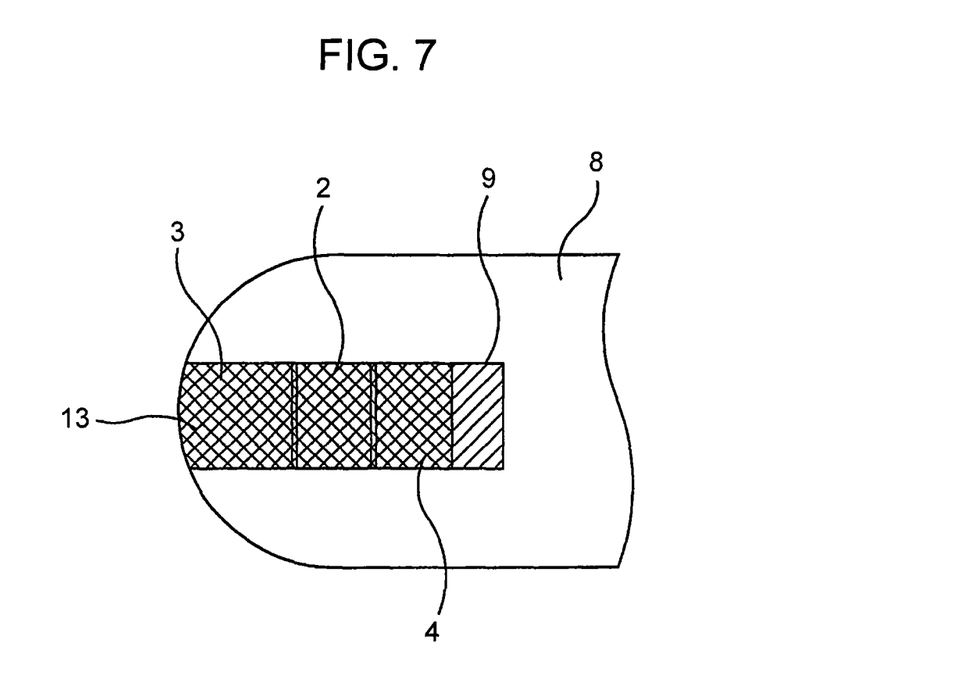
FIG. 7 is a drawing showing how a sample liquid is sufficiently introduced into an analyte feed passage.

However, such a biosensor has a problem. Counter electrode 3, measuring electrode 2, and detecting electrode 4 are disposed in proximity to one another. Thus, when an amount of sample liquid insufficient to fill analyte feed passage 7 is supplied as shown in FIGS. 5 and 6, for example, the sample liquid reaches detecting electrode 4 without completely covering measuring electrode 2 and then the measuring operation starts. This makes the response value lower than that given when the analyte feed passage is sufficiently filled with the sample liquid as shown in FIG. 7, thus deteriorating the performance of the biosensor. In the top views of FIGS. 5 through 7, reagent layer 5 is not shown for simplicity.

The present invention aims to address the above-mentioned problem. Therefore, it is an object of the present invention to improve accuracy of detecting the analyte by adding new ideas on the position and shape of the detecting electrode and to provide a high-performance biosensor having excellent accuracy of measurement.

DISCLOSURE OF INVENTION

In order to address the above-mentioned problem, according to one aspect of the present invention, there is provided a biosensor including:
- a first electrically insulated board and a second electrically insulated board;
  - an electrode system having at least a measuring electrode, a counter electrode, and a detecting electrode;
- an analyte feed passage for introducing the sample liquid over the electrode system; and
- a reagent used for quantifying a substrate contained in the sample liquid. The biosensor is characterized in that the electrode system, the analyte feed passage, and the reagent exist between the first electrically insulated board and the second electrically insulated board. The electrode system is formed on all or part of the inner surface of at least one of the first electrically insulated board and the second electrically insulated board. The detecting electrode is spaced from the measuring electrode by a distance sufficient for the sample liquid to sufficiently cover the measuring electrode before the sample liquid reaches the detecting electrode.

The detecting electrode of this biosensor can be shaped to project so that the central portion of the detecting electrode is positioned nearest to the measuring electrode within the analyte feed passage. Moreover, the detecting electrode can be shaped so that the both edges thereof are positioned farther from the measuring electrode than the central portion.

The detecting electrode can also be shaped to project in the direction of the inlet of the analyte feed passage in the central position of the analyte feed passage.

These shapes of the detecting electrode positioned within the analyte feed passage can be of V-shape, U-shape, or convex shape.

BEST MODE FOR CARRYING OUT OF THE INVENTION

A biosensor in accordance with an exemplary embodiment of the present invention is demonstrated hereinafter with reference to FIG. 1. Specifically described herein is an enzyme sensor using an enzyme as a molecule-identifying element that specifically reacts with a particular component in a sample liquid.

Figure 1A:
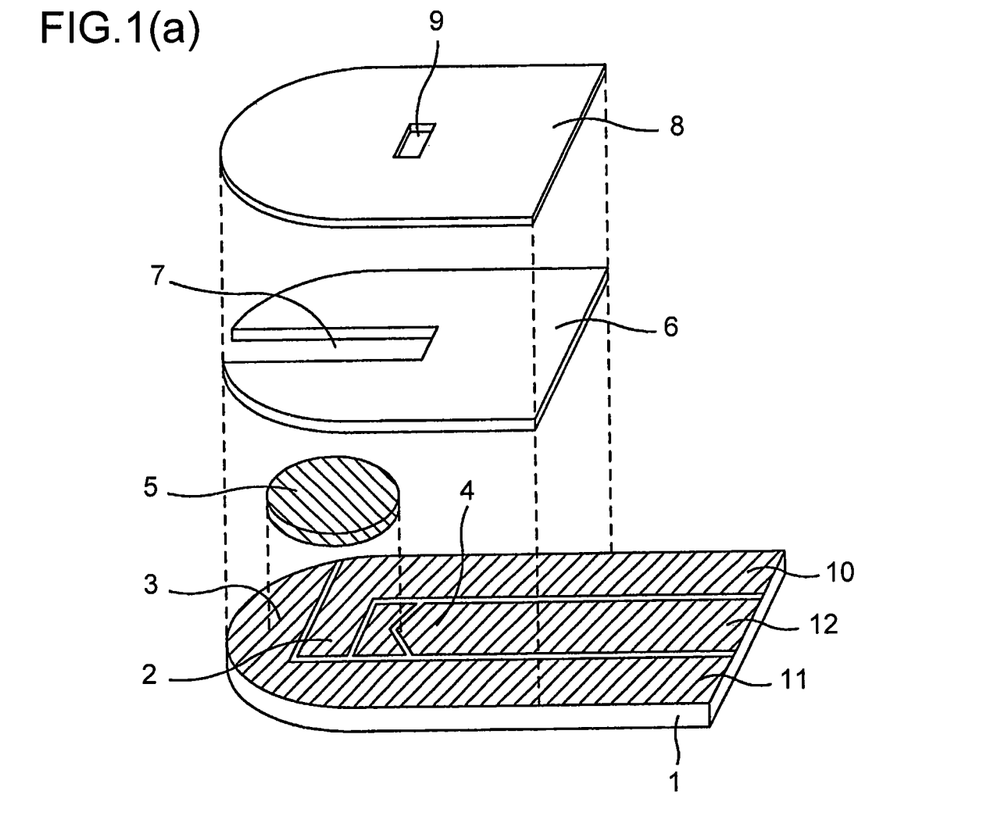
FIG. 1 is an exploded perspective view and a top view of a biosensor in accordance with an exemplary embodiment of the present invention.
Figure 1B:
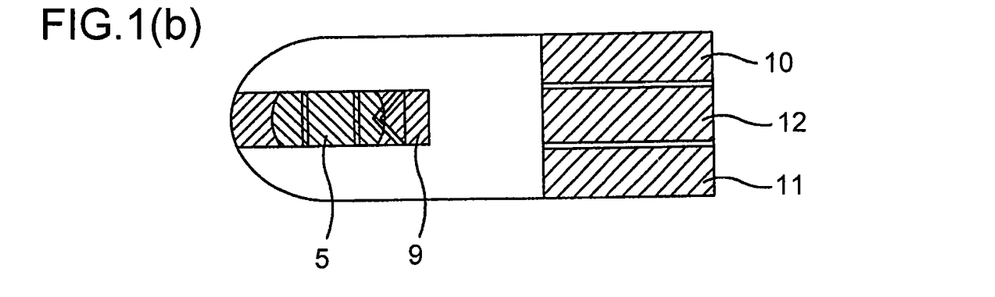

FIG. 1 is an exploded perspective view and a top view of a biosensor in accordance with this embodiment. In FIG. 1, reference numeral 1 shows a first electrically insulated board. Formed on this first electrically insulated board 1 are measuring electrode 2, counter electrode 3, and detecting electrode 4 that are made of electrically conductive materials.

In this embodiment, what largely differs from a conventional biosensor is that detecting electrode 4 having a predetermined shape is spaced from counter electrode 3 and measuring electrode 2 by a predetermined distance in analyte feed passage 7.

This predetermined distance means a distance sufficient for the sample liquid to completely cover measuring electrode 2 after the sample liquid is fed into analyte feed passage 7 before reaching detecting electrode 4. This distance can be set arbitrarily according to the width of the analyte feed passage.

As for the predetermined shape, it is desirable that detecting electrode 4 is shaped to lie nearest to the measuring electrode 2 in the central portion of analyte feed passage 7 and farther to the measuring electrode along the both edges of analyte feed passage 7 than in the central portion thereof. These shapes include a V-shape, U-shape, and convex shape, and combinations thereof. Among these shapes, a V-shape is most preferable.

Because the detecting electrode has such a distance and shape, measurement of a sample liquid starts after the liquid has completely covered the measuring electrode. When an amount of sample liquid insufficient to completely cover measuring electrode 2 is supplied as shown in FIGS. 4 and 5, erroneous start of measurement can be prevented. Moreover, for the above-mentioned shape of detecting electrode 4, the detecting electrode can be disposed nearer to the measuring electrode. Therefore, the amount of sample liquid necessary for the biosensor to measure can be reduced.

Figure 2A:
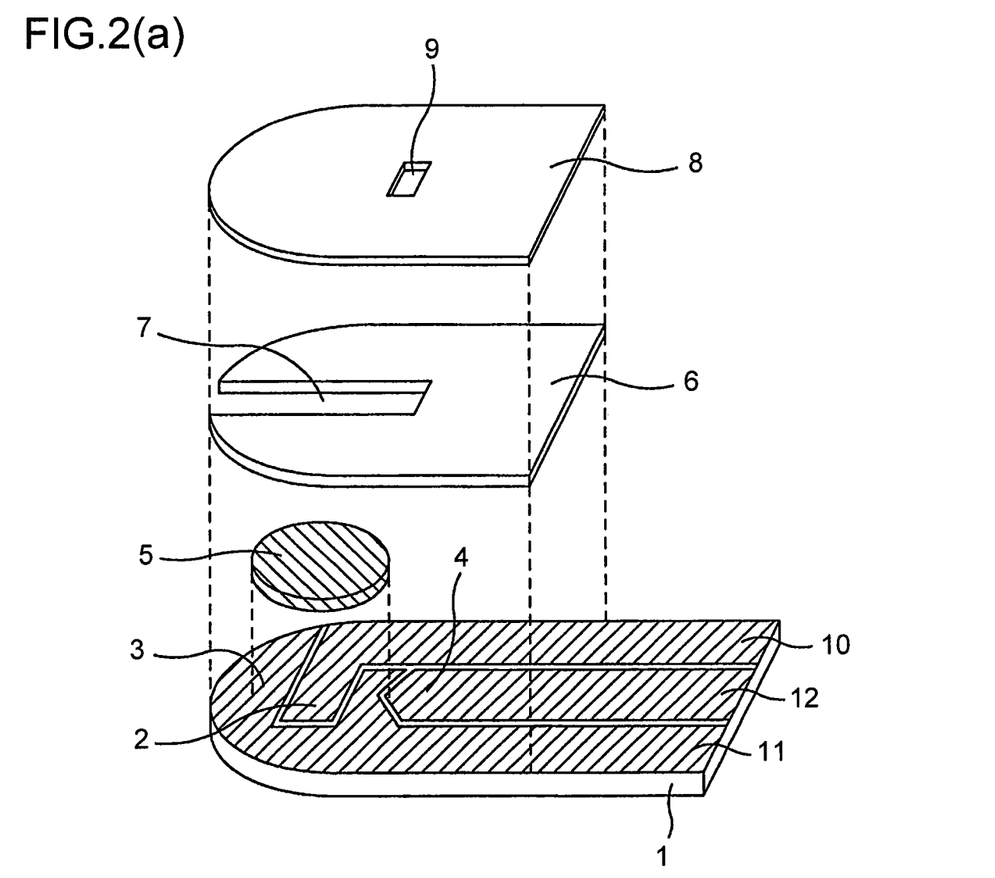
FIG. 2 is an exploded perspective view and a top view showing an example of another biosensor in accordance with an exemplary embodiment of the present invention.
Figure 2B:
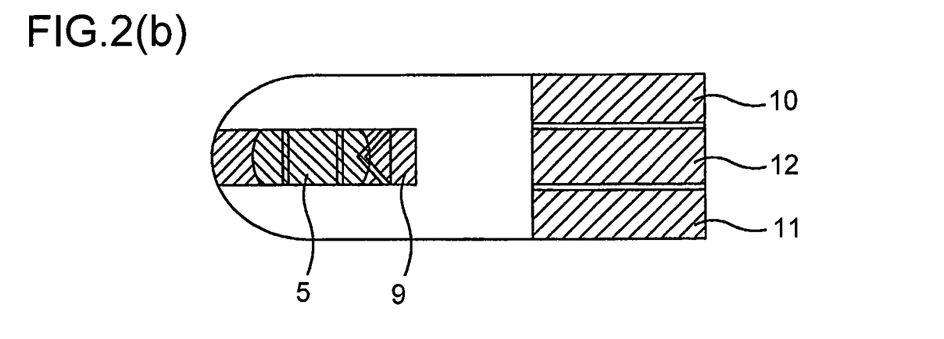

In the biosensor of FIG. 1, the space between measuring electrode 2 and detecting electrode 4 does not work as an electrode. However, as shown in FIG. 2, the space can be utilized as a part of counter electrode 3.

Moreover, detecting electrode 4 described herein can be used as a part of the counter electrode, as well as working as an electrode for detecting an insufficient amount of analyte.

In the biosensor of FIG. 1, each of the electrodes is disposed on the first electrically insulated board. However, these electrodes can be divided and disposed not only on first electrically insulated board 1 but also on second electrically insulated board 8 opposed thereto.

Preferable materials of above-mentioned first electrically insulated board 1 and second electrically insulated board 8 include polyethylene terephthalate, polycarbonate, and polyimide.

Electrically conductive materials constituting each electrode include single materials, such as noble metals (e.g. gold, platinum, and palladium) and carbon, and composite materials, such as carbon pastes and noble metal pastes.

The electrically conductive layer can be formed on first electrically insulated board 1 or second electrically insulated board 8 easily by such a method as sputtering vapor deposition for the single materials, and by such a method as screen-printing for the composite materials.

Each of the electrodes can be formed separately by forming the electrically conductive layer on all or part of the surface of first electrically insulated board 1 or second electrically insulated board 8 by the above-mentioned sputtering vapor deposition and screen-printing and other methods, and subsequently providing slits therein using laser and other means. Similarly, the electrodes can be formed by screen-printing using a printing plate or mask having electrode patterns formed thereon in advance, sputtering vapor deposition, and other methods.

Formed on the electrodes formed in this manner is reagent layer 5 containing an enzyme, electron carrier, hydrophilic polymer, and the like.

Examples of the usable enzyme include glucose oxidase, lactate oxidase, cholesterol oxidase, cholesterol esterase, uricase, ascorbate oxidase, bilirubin oxidase, glucose dehydrogenase, and lactate dehydrogenase. Examples of the usable electron carrier include p-benzoquinone and derivatives thereof, phenazine methosulfate, methylene blue, and ferrocene and derivatives thereof as well as potassium ferricyanide.

Examples of the usable hydrophilic polymer include carboxymethyl cellulose, hydroxyethyl cellulose, hydroxypropyl cellulose, methyl cellulose, ethyl cellulose, ethyl hydroxyethyl cellulose, carboxymethyl ethyl cellulose, polyvinyl alcohol, polyvinyl pyrrolidone, polyamino acids (e.g. polylysine), polystyrene sulfonate, gelatin and derivatives thereof, acrylic acids and salts thereof, methacrylic acids and salts thereof, starch and derivatives thereof, maleic anhydrides and salts thereof, and agarose gel and derivatives thereof.

Next, the first electrically insulated board 1 and second electrically insulated board 8 are bonded to spacer 6 having a notch to form analyte feed passage 7 for receiving a sample liquid.

In order to reduce the amount of the sample liquid necessary for the biosensor to measure, it is desirable that analyte feed passage 7 has a width ranging from 0.5 to 2.0 mm and spacer 6 has a thickness (height) ranging from 0.05 to 0.3 mm.

Examples of the preferable material of spacer 6 include polyethylene terephthalate, polycarbonate, polyimide, polybutylene terephthalate, polyamide, polyvinyl chloride, polyvinyliden chloride, polyimide, and nylon.

Alternatively, integrated second electrically insulated board 8 and spacer 6 can be bonded to first electrically insulated board 1 to form analyte feed passage 7.

The reagent layer 5 can be placed in any position within analyte feed passage 7 for receiving the sample liquid as well as on all or part of the surface of the electrodes, on condition that the reagent layer will not deteriorate the performance of the biosensor.

However, in order to realize quick detection of the sample liquid after the supply thereof, it is desirable that reagent layer 5 exists on detecting electrode 4 or in the vicinity thereof.

The supply of a sample liquid to a biosensor structured of such analyte feed passage 7 is realized by capillarity. In order to realize smooth supply of the sample liquid, air vent 9 for letting the air escape outside of the biosensor must be provided within analyte feed passage 7.

Air vent 9 can be disposed in any position within analyte feed passage 7 on condition that the air vent will not hinder the supply of the sample liquid. Air vent 9 can be of any size that can let the air escape smoothly. When a small air vent is disposed within an analyte feed passage, the sample liquid is easily be lead along the edges of the analyte feed passage. Thus, the shape of the detecting electrode shown in FIG. 3 is most preferable.

Figure 3A:
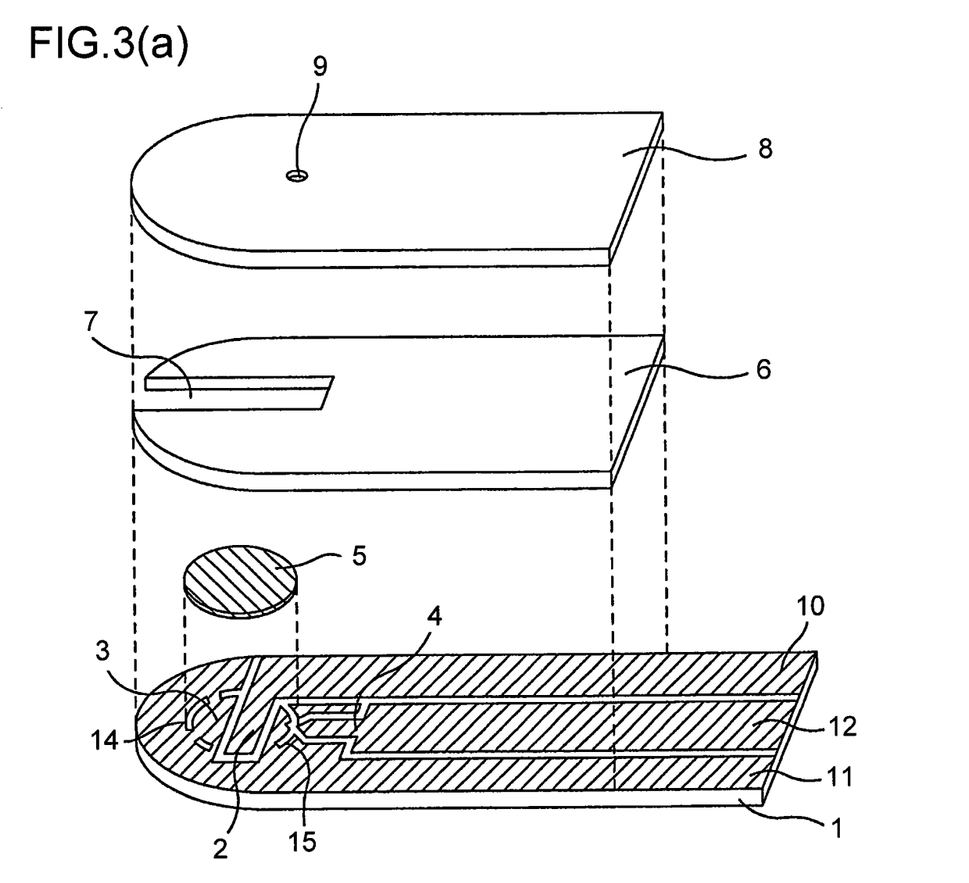
FIG. 3 is an exploded perspective view and a top view showing an example in accordance with an exemplary embodiment of the present invention that has an air vent disposed within an analyte feed passage.
Figure 3B:
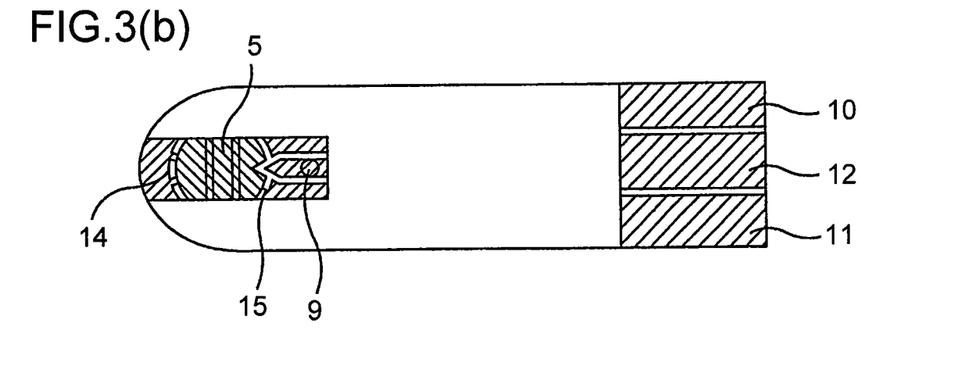

In the biosensor of FIG. 3, arc slits are formed around the reagent dropping position. Specifically, by providing a wave-like arc slit 14 on the tip side of the sensor and slit 15 on the back side of the feed passage, propagation of the reagent is easily controlled in formation of reagent layer 5. These arc slits are more effective in controlling the reagent than the arc slit disclosed in the above-mentioned PCT patent application.

In addition, rendering hydrophilic nature to the inner surface of the analyte feed passage 7 allows quicker and more accurate introduction of the sample liquid into analyte feed passage 7.

The methods of rendering hydrophilic nature include applying surface-active agent to first electrically insulated board 1 or second electrically insulated board 8 itself, or the surface thereof, and roughening the surface of the board material by sandblasting, electric-discharge machining, non-glare treatment, matting, chemical plating, or the like.

Described hereinafter is a system of checking for suction of an analyte when the content of a substrate in a sample liquid, i.e. the analyte, is determined using a biosensor of such a structure.

First, a sample liquid is fed to the inlet of the analyte feed passage while a constant voltage is applied between the counter electrode or the measuring electrode and the detecting electrode by a measuring device (not shown) coupled to the biosensor. The sample liquid is sucked into the analyte feed passage by capillarity, passes over the counter electrode and the measuring electrode, and reaches the detecting electrode. Then, dissolution of the reagent layer starts. At this time, the measuring device detects electrical changes occurring between the counter electrode or the measuring electrode and the detecting electrode and starts measuring operation.

In this embodiment, an enzyme sensor is described as an example of a biosensor. However, the present invention can similarly be applied to a biosensor that uses an antibody, microorganism, DNA, RNA, or the like as well as the enzyme as a molecule-identifying element specifically reacting with a particular component in the sample liquid.

INDUSTRIAL APPLICABILITY

As mentioned above, the present invention can drastically improve the accuracy of detecting the introduction of a sample liquid into an analyte feed passage using a detecting electrode. The present invention can also provide a high-performance biosensor causing less error of measurement. Furthermore, the sample liquid necessary for the biosensor to measure can be reduced. These advantages can provide a biosensor that has high user operability and can deal with a small amount of analyte.

The invention claimed is:

1. A biosensor for quantifying a substrate contained in a sample liquid comprising:
   a first insulating support;
   a second insulating support;
   an electrode system having at least a measuring electrode, a counter electrode including a first portion and a second portion, and a detecting electrode;
   a spacer configured to define a specimen supply path for introducing the sample liquid over the electrode system;
   wherein the electrode system is arranged from a tip of the specimen supply path to a downstream portion of the specimen supply path in a following order: the first portion of the counter electrode, the measuring electrode, the second portion of the counter electrode and the detecting electrode;
   wherein the second insulating support has an air hole which is formed over a downstream portion of the detecting electrode; and
   wherein, in a planer view, a tip of the detecting electrode positioned within the specimen supply path has a V-shape and is covered by the second insulating support, and the downstream portion of the detecting electrode is exposed to the air hole.

2. The biosensor as set forth in claim 1, wherein said air hole is formed only over the detecting electrode.

3. The biosensor as set forth in claim 1, wherein said tip of the detecting electrode having the V-shape is shaped to project in a direction of an inlet of said specimen supply path in a central position within said specimen supply path.

4. The biosensor as set forth in claim 1, wherein said specimen supply path has a width ranging from 0.5 to 2.0 mm.

5. The biosensor as set forth in claim 1, wherein said specimen supply path has a height ranging from 0.05 to 0.3 mm.

6. The biosensor as set forth in claim 1, wherein said electrode system is divided by providing a slit in an electrically conductive layer formed on one of all and part of an inner surface of at least one of said first electrically insulating support and said second electrically insulating support.

7. The biosensor as set forth in claim 6, wherein said slit is formed by machining the electrically conductive layer using a laser.

8. The biosensor as set forth in claim 3, wherein said electrode system is divided by providing a slit in an electrically conductive layer formed on one of all and part of an inner surface of at least one of said first electrically insulating support and said second electrically insulating support.

9. The biosensor as set forth in claim 1, wherein the detecting electrode is shaped such that the central portion is positioned adjacent to each edge portion such that each edge portion of the detecting electrode is positioned nearer to the path boundary of the specimen supply path and farther from the measuring electrode than the central portion of the detecting electrode.

10. A biosensor according to claim 1, wherein a back edge of said counter electrode is closer to said measuring electrode at said center axis than said back edge of said counter electrode away from said center axis.

11. A biosensor according to claim 1, wherein the air hole does not extend to an upstream side of said detecting electrode.

12. The biosensor according to claim 1, wherein the measuring electrode, the first and second portions of the counter electrode and the detecting electrode are disposed to perpendicularly intersect an inflow direction of the sample liquid in the specimen supply path.

13. A biosensor for quantifying a substrate contained in a sample liquid comprising:
   a first insulating support;
   a second insulating support;
   a plurality of electrodes disposed between the first insulating support and the second insulating support, the plurality of electrodes including at least a measuring electrode, a counter electrode including a first portion and a second portion, and a detecting electrode;

a spacer disposed between the second insulating support and the plurality of electrodes, the spacer configured to define a specimen supply path for introducing the sample liquid over the plurality of electrodes from an upstream portion of the specimen supply path to a downstream portion of the specimen supply path;

wherein the plurality of electrodes are arranged from the upstream portion of the specimen supply path to the downstream portion of the specimen supply path in a following order: the first portion of the counter electrode, the measuring electrode, the second portion of the counter electrode and the detecting electrode;

wherein the second insulating support includes an air hole arranged over a first portion of the detecting electrode; and wherein, in a planer view, a second portion of the detecting electrode has a V-shape and is covered by the second insulating support, the second portion of the detecting electrode being disposed further upstream along the specimen supply path than the first portion of the detecting electrode.

14. The biosensor as set forth in claim 13, wherein said air hole is formed only over the detecting electrode.

* * * * *